US012558079B2

(12) United States Patent
Helgeson et al.

(10) Patent No.: US 12,558,079 B2
(45) Date of Patent: Feb. 24, 2026

(54) CATHETER INCLUDING WIRE MANAGEMENT CAP AND METHODS OF ASSEMBLING SAME

(71) Applicant: St. Jude Medical, Cardiology Division, Inc., St. Paul, MN (US)

(72) Inventors: Zachary L. Helgeson, Richfield, MN (US); Michael Bowers, Edina, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 995 days.

(21) Appl. No.: 17/766,841

(22) PCT Filed: Sep. 28, 2020

(86) PCT No.: PCT/US2020/053137

§ 371 (c)(1),
(2) Date: Apr. 6, 2022

(87) PCT Pub. No.: WO2021/071692

PCT Pub. Date: Apr. 15, 2021

(65) Prior Publication Data

US 2024/0081795 A1     Mar. 14, 2024

Related U.S. Application Data

(60) Provisional application No. 62/911,537, filed on Oct. 7, 2019.

(51) Int. Cl.
*A61M 25/01*        (2006.01)
*A61B 17/00*        (2006.01)
(Continued)

(52) U.S. Cl.
CPC .... *A61B 17/00234* (2013.01); *A61B 18/1492* (2013.01); *A61M 25/0136* (2013.01);
(Continued)

(58) Field of Classification Search
CPC .......... A61M 25/0133; A61M 25/0136; A61M 25/0147; A61B 2018/0091
See application file for complete search history.

(56) References Cited

U.S. PATENT DOCUMENTS 9,149,607 B2 * 10/2015 Scheibe ............ A61M 25/0147
2015/0094654 A1    4/2015 Bansal et al.

FOREIGN PATENT DOCUMENTS

WO        9707848        3/1997
WO        02087455 A1   11/2002
(Continued)

OTHER PUBLICATIONS

International Search Report and Written Opinion, PCT/US2020/053137, mailing date: Dec. 11, 2020, 10 pages.

*Primary Examiner* — Laura A Bouchelle
(74) *Attorney, Agent, or Firm* — Wiley Rein LLP

(57)        ABSTRACT

A catheter handle includes a housing extending from a proximal end to a distal end along a longitudinal axis. The housing defines an internal cavity. The catheter handle also includes at least one wire extending through the internal cavity between the proximal end and the distal end. The catheter handle further includes a wire management cap positioned within the internal cavity between a movable component of the catheter handle and one of the proximal and distal ends. The wire management cap defines a wire receiver cavity sized to receive a portion of the wire therein. The wire management cap is oriented such that the portion of the wire in the wire receiver cavity is separated from the movable component by the wire management cap to prevent interference between the movable component and the wire.

19 Claims, 15 Drawing Sheets

(51) Int. Cl.
   *A61B 18/14*           (2006.01)
   *A61B 18/00*           (2006.01)

(52) U.S. Cl.
   CPC ............... *A61B 2017/00323* (2013.01); *A61B 2018/0091* (2013.01)

(56)                References Cited

FOREIGN PATENT DOCUMENTS

| WO | 2015094654 | A1 | 6/2015 |
| WO | 2017115310 | A1 | 7/2017 |

* cited by examiner

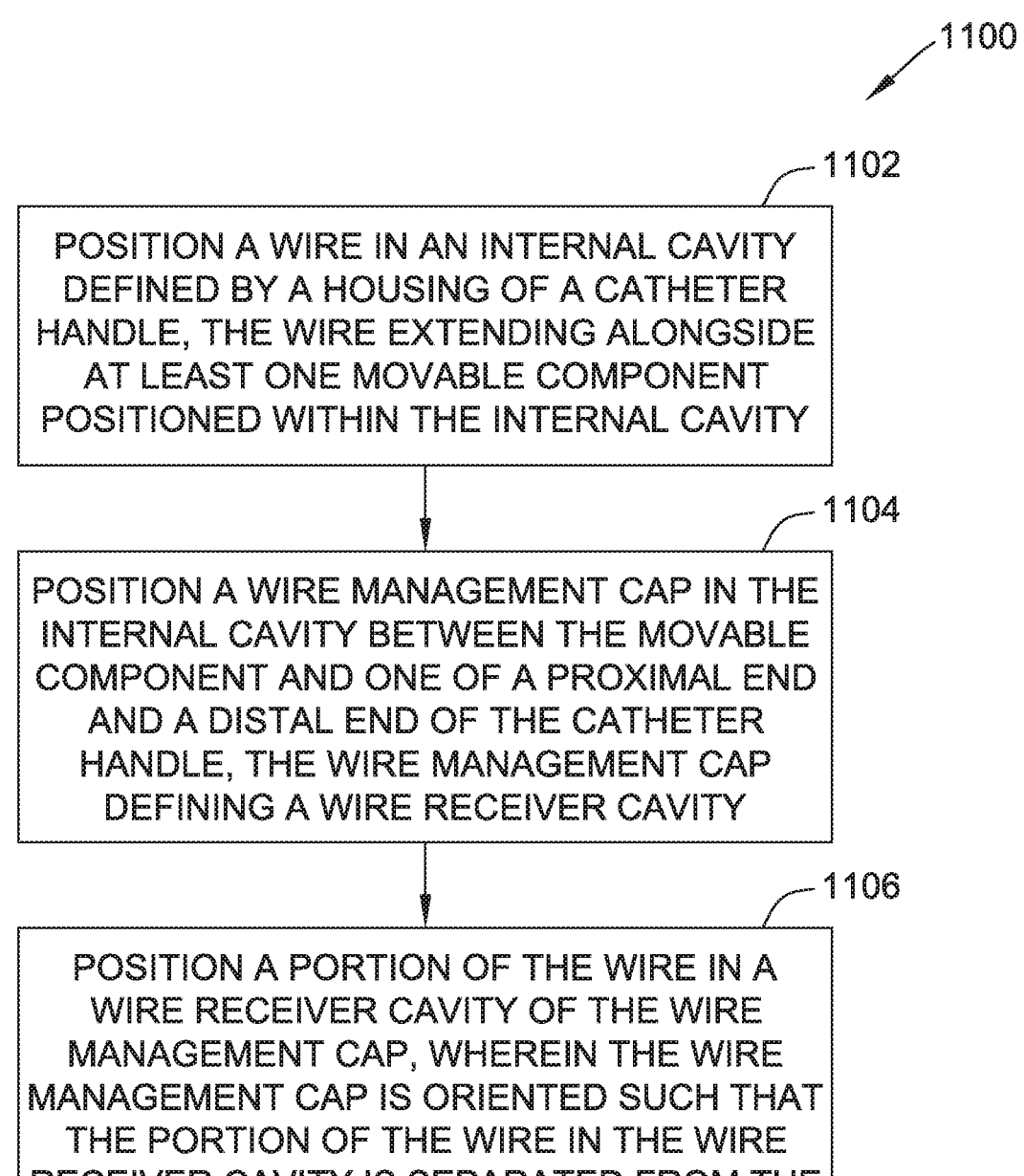

1100

1102

POSITION A WIRE IN AN INTERNAL CAVITY DEFINED BY A HOUSING OF A CATHETER HANDLE, THE WIRE EXTENDING ALONGSIDE AT LEAST ONE MOVABLE COMPONENT POSITIONED WITHIN THE INTERNAL CAVITY

1104

POSITION A WIRE MANAGEMENT CAP IN THE INTERNAL CAVITY BETWEEN THE MOVABLE COMPONENT AND ONE OF A PROXIMAL END AND A DISTAL END OF THE CATHETER HANDLE, THE WIRE MANAGEMENT CAP DEFINING A WIRE RECEIVER CAVITY

1106

POSITION A PORTION OF THE WIRE IN A WIRE RECEIVER CAVITY OF THE WIRE MANAGEMENT CAP, WHEREIN THE WIRE MANAGEMENT CAP IS ORIENTED SUCH THAT THE PORTION OF THE WIRE IN THE WIRE RECEIVER CAVITY IS SEPARATED FROM THE MOVABLE COMPONENT BY THE WIRE MANAGEMENT CAP TO PREVENT INTERFERENCE BETWEEN THE MOVABLE COMPONENT AND THE WIRE

FIG. 19

CATHETER INCLUDING WIRE MANAGEMENT CAP AND METHODS OF ASSEMBLING SAME

CROSS-REFERENCE TO RELATED APPLICATIONS

This application claims priority to international application No. PCT/US2020/053137, filed Sep. 28, 2020, which claims priority to U.S. Provisional Patent Application Ser. No. 62/911,537 filed Oct. 7, 2019, the disclosure of which is hereby incorporated by reference in its entirety.

BACKGROUND OF THE DISCLOSURE

Field of the Disclosure

The present disclosure relates generally to medical devices that are used in the human body. More particularly, the present disclosure relates to catheters including a wire management cap, and methods of assembling such catheters.

Background

Medical devices, such as, for example, mapping, electroporation, and/or electrophysiology catheters, are used in a variety of diagnostic and/or therapeutic medical procedures. In some procedures, a catheter is manipulated through a patient's vasculature to a patient's heart, for example, and carries one or more electrodes that may be used for mapping, ablation, diagnosis, and/or to perform other functions. Typical catheters include a catheter shaft that connects to a catheter handle at a proximal end and carries the electrodes at a distal end. The catheter shaft is inserted into the patient's vasculature for delivering the electrodes to an intended site. Once at the intended site, treatment may include radio frequency (RF) ablation, cryoablation, lasers, chemicals, high-intensity focused ultrasound, etc. As is readily apparent, such treatment requires precise control of the catheter during manipulation to, from, and at a mapping and/or treatment site, which can invariably be a function of a user's skill level. Typical catheters include an actuator assembly on the handle for manipulating the catheter shaft through the patient's vasculature and positioning the electrodes at the intended site.

In conventional catheters, the handle includes movable components, wires, electronic components, and various other parts that are housed within an internal cavity of a housing of the handle. Due to limited space within the internal cavity, components within the handle are often positioned within close proximity to one another and, if adequate measures are not implemented, may interfere with one other during operation of the catheter. For example, wires may extend through the internal cavity alongside movable components, and the wires and movable components may interfere with each other during operation of the catheter. Moreover, it is generally not desirable to increase the size of the catheter handle, as this may make the catheter more difficult to handle and operate. As a result, catheters may be expensive and complicated to assemble because each part must be carefully positioned relative to other parts within the internal cavity to limit interference between the parts.

Accordingly, a need exists for improved catheters that have increased reliability during operation and are simpler to assemble. In addition, there is a need for catheters having a compact shape and size.

SUMMARY OF THE DISCLOSURE

In one aspect, a catheter handle includes a housing extending from a proximal end to a distal end along a longitudinal axis. The housing defines an internal cavity. The catheter handle also includes at least one wire extending through the internal cavity between the proximal end and the distal end. The catheter handle further includes a wire management cap positioned within the internal cavity between a movable component of the catheter handle and one of the proximal and distal ends. The wire management cap defines a wire receiver cavity sized to receive a portion of the wire therein. The wire management cap is oriented such that the portion of the wire in the wire receiver cavity is separated from the movable component by the wire management cap to prevent interference between the movable component and the wire.

In another aspect, a catheter includes a handle extending from a proximal end to a distal end along a longitudinal axis. The handle includes a housing defining an internal cavity. The catheter also includes a catheter shaft attached to the distal end of the handle. The catheter shaft includes at least one wire that extends into and through the internal cavity. The catheter further includes an actuator assembly including at least one movable component disposed in the internal cavity. The catheter also includes a wire management cap positioned within the internal cavity and defining a wire receiver cavity sized to receive a portion of the wire therein. The wire management cap is oriented such that the portion of the wire in the wire receiver cavity is separated from the movable component by the wire management cap to prevent interference between the movable component and the wire.

In yet another aspect, a method of assembling a catheter handle includes positioning a wire in an internal cavity defined by a housing of the catheter handle. The wire extends alongside at least one movable component positioned within the internal cavity. The method also includes positioning a wire management cap in the internal cavity between the movable component and one of a proximal end and a distal end of the catheter handle. The wire management cap defines a wire receiver cavity. The method further includes positioning a portion of the wire in a wire receiver cavity of the wire management cap. The wire management cap is oriented such that the portion of the wire in the wire receiver cavity is separated from the movable component by the wire management cap to prevent interference between the movable component and the wire.

BRIEF DESCRIPTION OF THE DRAWINGS

FIG. 19 is a flow diagram illustrating one embodiment of a method of assembling a catheter.

DETAILED DESCRIPTION OF THE DISCLOSURE

Figure 1:
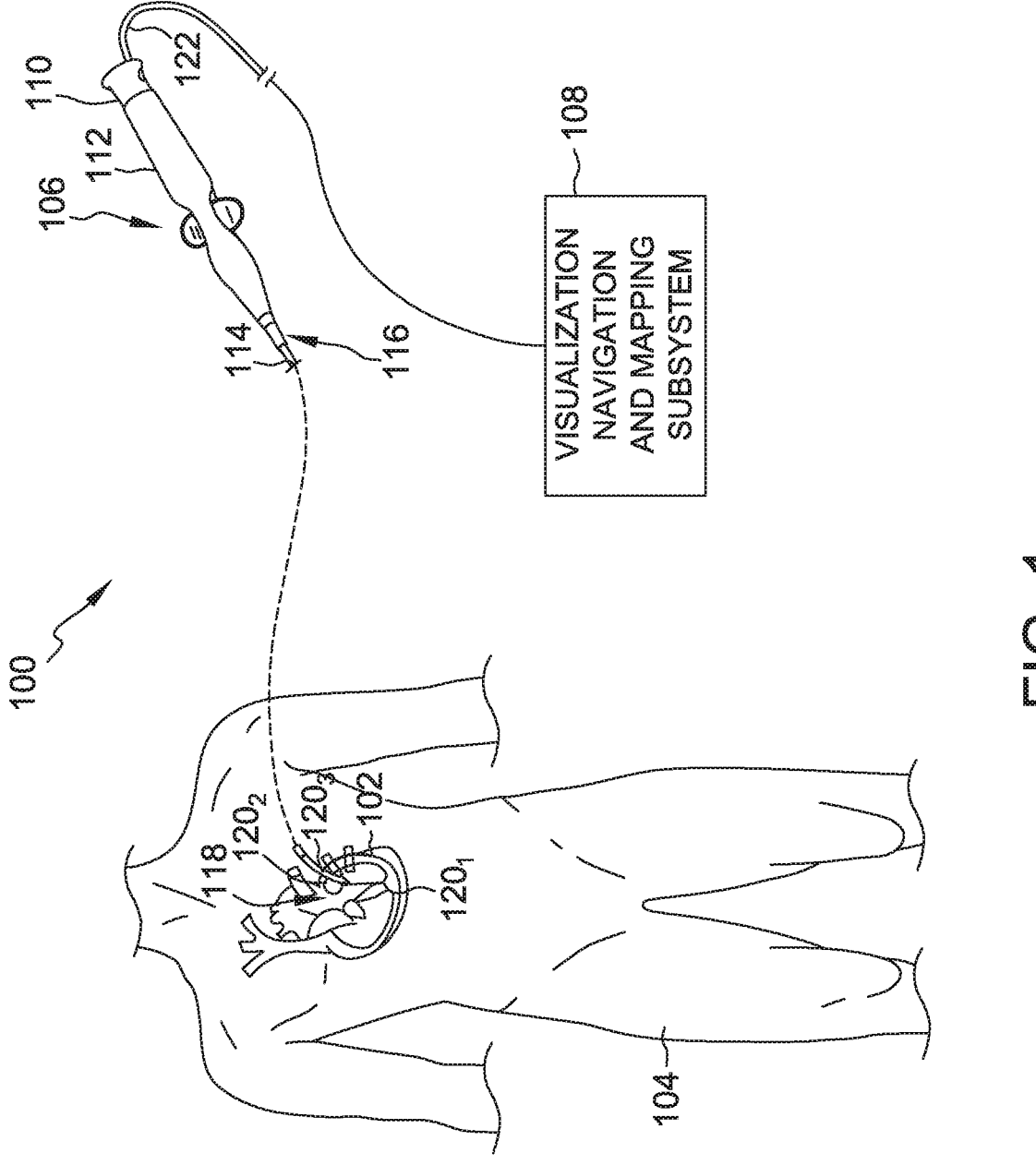
FIG. 1 is a schematic and block diagram view of a system for performing one or more diagnostic and/or therapeutic functions including a catheter.

The present disclosure is directed to a catheter including at least one wire management feature. For example, the catheter may include a wire management cap positioned within the internal cavity of a catheter handle. The wire management cap is positioned within the internal cavity between a movable component of the catheter handle and a proximal end of the catheter handle. The wire management cap defines a wire receiver cavity sized to receive a portion of the wire therein. For example, the wire cavity receives one or more loops or gatherings of wire to retain the wire in a desired position and reduce the amount of slack wire in the internal cavity. Accordingly, the wire is able to have a length that is greater than the straight-line distance between components which allows the wire to be connected to terminals of the catheter handle during assembly of the catheter without interference between the extra length of wire and other components in the internal cavity. In addition, the wire management cap can simplify assembly of the catheter because the portion of the wire in the wire receiver cavity can be positioned precisely within the internal cavity while the wire is in the wire receiver cavity and then retained in position without the use of additional attachment means.

In some embodiments, the wire management cap is oriented such that the portion of the wire in the wire receiver cavity is separated from one or more movable components by the wire management cap to prevent interference between the movable components and the wire. For example, the wire may be retained by the wire management cap such that the wire is not in a range of movement of the movable components. Additionally or alternatively, the wire management cap may include one or more walls that physically separates the wire from the movable components. Accordingly, the wire management cap prevents the wire from contacting and impeding movement of the movable components. In addition, the wire management cap prevents the movable components from displacing the wire, which might otherwise cause the wires to disconnect from electrical components. Moreover, the wire management cap separates the movable components and the wires to prevent the movable components and the wires from damaging each other during operation of the catheter.

Also, in some embodiments, the wire management cap includes engagement structures that allow the wire management cap to attach to a housing of the catheter handle without other attachment means. For example, engagement structures on the housing and the wire management cap may allow a press-fit engagement between the wire management cap and the housing when the wire management cap is positioned in the internal cavity at a desired axial position. Accordingly, because the wire management cap is manually attachable to the housing (i.e., by hand), the wire management cap may simplify assembly of the catheter. In addition, the wire management cap is held in position by the engagement structures to reduce movement of the wire management cap during operation of the catheter.

Moreover, the size of the catheter may be reduced in comparison to other catheters because the wire management cap allows the wires and the movable components to be positioned in closer proximity to each other than other catheters without risk of interference between the wire and the components.

In some embodiments, the catheter as described herein is a unidirectional catheter. That is, the catheter shaft is deflectable in only a single direction. In other embodiments, the catheter is a bidirectional catheter. That is, the catheter shaft is deflectable in at least two different directions.

Referring now to the drawings, FIG. 1 illustrates one exemplary embodiment of a system 100 for performing one or more diagnostic and/or therapeutic functions on or for a tissue 102 of a body 104. In an exemplary embodiment, tissue 102 includes heart or cardiac tissue within a human body 104. It should be understood, however, that system 100 may find application in connection with a variety of other tissues within human and non-human bodies, and therefore, the present disclosure is not meant to be limited to the use of system 100 in connection with only cardiac tissue and/or human bodies.

System 100 may include a medical device (e.g., a catheter 106) and a subsystem 108 for the visualization, navigation, and/or mapping of internal body structures (hereinafter referred to as the "visualization, navigation, and mapping subsystem 108", "subsystem 108", or "mapping system").

In this embodiment, the medical device includes a catheter 106, such as, for example, an electrophysiology catheter. In other exemplary embodiments, the medical device may take a form other than catheter 106, such as, for example and without limitation, a sheath or catheter-introducer, or a catheter other than an electrophysiology catheter. For clarity and illustrative purposes only, the description below will be limited to embodiments of system 100 wherein medical device is a catheter (catheter 106).

Catheter 106 is provided for examination, diagnosis, and/or treatment of internal body tissues such as tissue 102. Catheter 106 may include a wire connector 110 or interface, a handle 112, a shaft 114 having a proximal end 116 and a distal end 118 (as used herein, "proximal" refers to a direction toward the end of catheter 106 at handle 112 and away from body 104, and "distal" refers to a direction away from handle 112 and towards the end of catheter 106 introduced into body 104), and one or more sensors, such as, for example and without limitation, a plurality of electrodes 120 (i.e., 120₁, 120₂, . . . , 120_N), mounted in or on shaft 114 of catheter 106 at or near distal end 118 of shaft 114. Distal end 118 of catheter 106 may include a distal loop subassembly, such as distal loop subassembly 228 (shown in FIG. 2).

In other embodiments, catheter 106 may further include other conventional components such as, for example and without limitation, steering wires and actuators, irrigation lumens and ports, pressure sensors, contact sensors, temperature sensors, additional electrodes and corresponding conductors or leads, and/or ablation elements (e.g., ablation electrodes, high intensity focused ultrasound ablation elements, and the like).

Handle 112 provides a location for the operator to hold catheter 106 and may further provide means for steering or guiding shaft 114 within the patient. For example, handle 112 may include means to change the length of a guidewire extending through catheter 106 to distal end 118 of shaft 114 to steer shaft 114. It will be appreciated by those of skill in the art that the construction of handle 112 may vary.

As described further herein, handle 112 may include one or more wire management features for one or more wires (not shown in FIG. 1) extending through handle 112. For example, wire management features may retain the wires in position within the handle 112 and prevent interference between the wires and one or more movable components of the handle 112.

Connector 110 provides mechanical and electrical connection(s) for the one or more wires 122 extending, for example, from visualization, navigation, and mapping subsystem 108 to one or more sensors mounted on catheter 106. In other embodiments, connector 110 may also provide mechanical, electrical, and/or fluid connections for wires extending from other components in system 100, such as, for example, an ablation system and a fluid source (when catheter 106 includes an irrigated catheter). Connector 110 is disposed at proximal end 116 of catheter 106.

In another exemplary embodiment, catheter 106 may be robotically driven or controlled. Accordingly, rather than an operator manipulating a handle to steer or guide catheter 106, and shaft 114 thereof, in particular, a robot is used to manipulate catheter 106.

Shaft 114 is generally an elongated, tubular, flexible member configured for movement within the patient. Shaft 114 supports, for example and without limitation, electrodes 120, associated conductors, and possibly additional electronics used for signal processing or conditioning. Shaft 114 may also permit transport, delivery and/or removal of fluids (including irrigation fluids, cryogenic ablation fluids, and bodily fluids), medicines, and/or surgical tools or instruments. Shaft 114 may be made from conventional materials such as polyurethane, and defines one or more lumens configured to house and/or transport at least electrical conductors, fluids, or surgical tools. Shaft 114 may be introduced into cardiac tissue 102 through a conventional introducer. Shaft 114 may then be steered or guided within cardiac tissue 102 to a desired location with guidewires or other means known in the art.

Visualization, navigation, and mapping subsystem 108 may be used to determine the positions of electrodes 120 or other sensors. These positions may be projected onto a geometrical anatomical model. In some embodiments, visualization, navigation, and mapping subsystem 108 includes a magnetic field-based system. For example visualization, navigation, and mapping subsystem 108 may include an electrical field- and magnetic field-based system such as the ENSITE PRECISION™ system commercially available from Abbott Laboratories, and generally shown with reference to U.S. Pat. No. 7,263,397 entitled "Method and Apparatus for Catheter Navigation and Location and Mapping in the Heart", the entire disclosure of which is incorporated herein by reference. In such embodiments, distal end 118 may include at least one magnetic field sensor—e.g., magnetic coils (not shown). If two or more magnetic field sensors are utilized, a full six-degree-of-freedom registration of magnetic and spatial coordinates could be accomplished without having to determine orthogonal coordinates by solving for a registration transformation from a variety of positions and orientations. Further benefits of such a configuration may include advanced dislodgement detection and deriving dynamic field scaling since they may be self-contained.

In other exemplary embodiments, subsystem 108 may utilize systems other than electric field-based systems. For example, subsystem 108 may include a magnetic field-based system such as the CARTO™ system commercially available from Biosense Webster, and as generally shown with reference to one or more of U.S. Pat. No. 6,498,944 entitled "Intrabody Measurement"; U.S. Pat. No. 6,788,967 entitled "Medical Diagnosis, Treatment and Imaging Systems"; and U.S. Pat. No. 6,690,963 entitled "System and Method for Determining the Location and Orientation of an Invasive Medical Instrument," the disclosures of which are incorporated herein by reference in their entireties.

In yet another exemplary embodiment, subsystem 108 may include a magnetic field-based system such as the GMPS system commercially available from MediGuide Ltd., and as generally shown with reference to one or more of U.S. Pat. No. 6,233,476 entitled "Medical Positioning System"; U.S. Pat. No. 7,197,354 entitled "System for Determining the Position and Orientation of a Catheter"; and U.S. Pat. No. 7,386,339 entitled "Medical Imaging and Navigation System," the disclosures of which are incorporated herein by reference in their entireties.

In a further exemplary embodiment, subsystem 108 may utilize a combination electric field-based and magnetic field-based system as generally shown with reference to U.S. Pat. No. 7,536,232 entitled "Hybrid Magnetic-Based and Impedance Based Position Sensing," the disclosure of which is incorporated herein by reference in its entirety. In yet still other exemplary embodiments, the subsystem 108 may comprise or be used in conjunction with other commonly available systems, such as, for example and without limitation, fluoroscopic, computed tomography (CT), and magnetic resonance imaging (MRI)-based systems.

Although not shown in FIG. 1, in some embodiments, system 100 may include suitable components to perform electroporation and/or ablation (e.g., RF ablation). It should be understood that in such embodiments, variations are possible as to the type of ablation energy provided (e.g., cryoablation, ultrasound, etc.).

Figure 2:
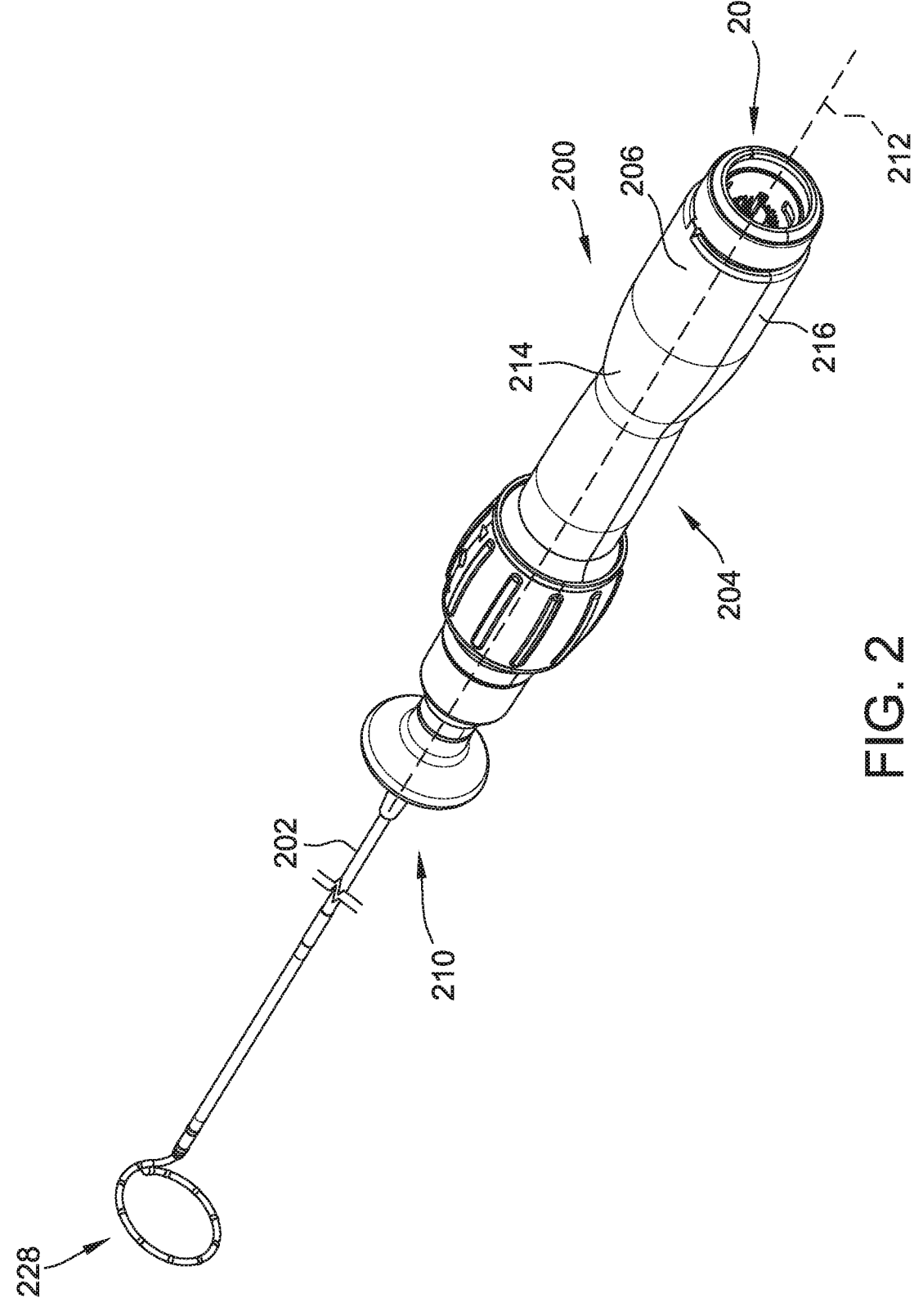
FIG. 2 is a perspective view of one embodiment of a catheter for use with the system of FIG. 1, the catheter including a catheter handle.
Figure 3:
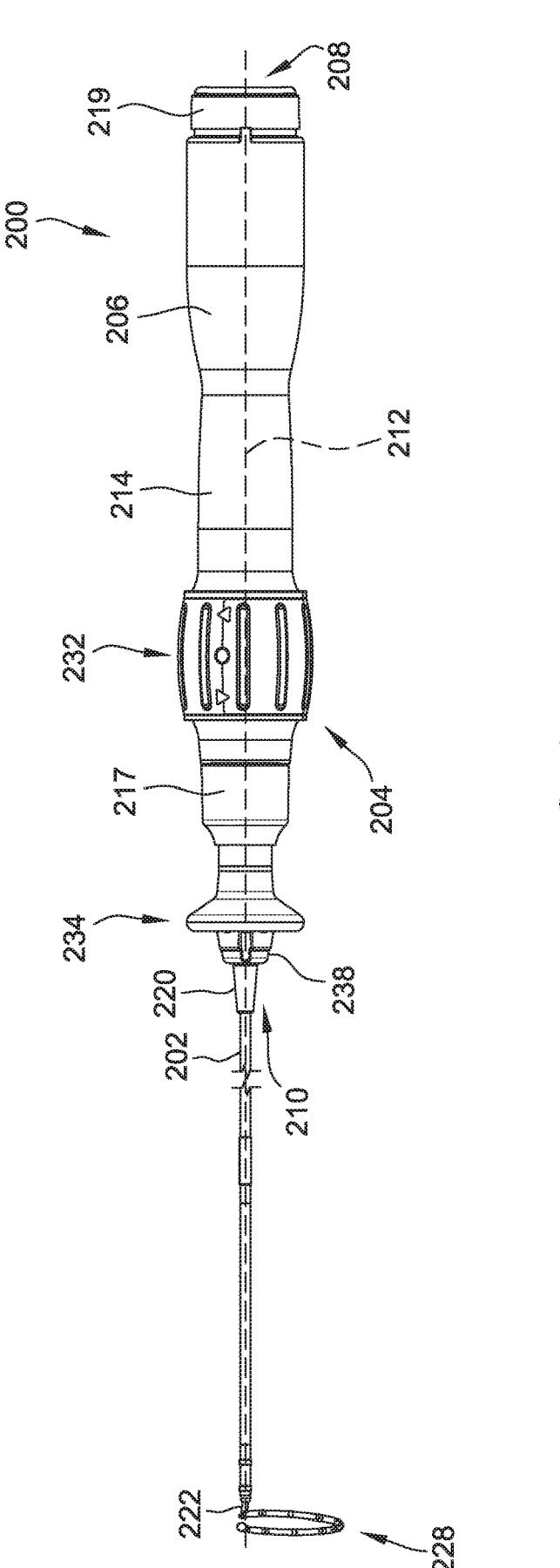
FIG. 3 is a top view of the catheter of FIG. 2.

FIGS. 2 and 3 illustrate one exemplary embodiment of a catheter 200 suitable for use with system 100 shown in FIG. 1. As used herein, the term catheter includes, without limitation, catheters, sheaths, and similar medical devices. As shown in FIGS. 2 and 3, catheter 200 includes an elongated, flexible, generally cylindrical hollow shaft 202 and an ergonomically shaped actuation handle 204.

Figure 4:
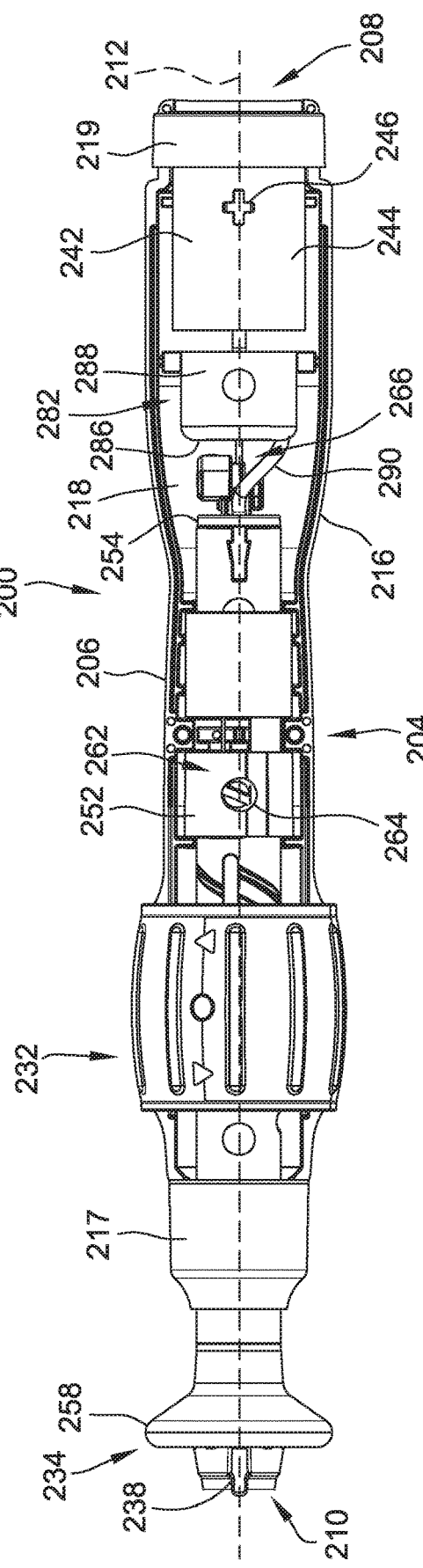
FIG. 4 is a top view of a portion of the catheter of FIG. 2 with a grip portion removed to illustrate an internal cavity of the catheter handle.

As shown in FIGS. 2-4, actuation handle 204 includes a housing 206 extending from a proximal end 208 to a distal end 210 along a longitudinal axis 212. Housing 206 includes an upper grip portion 214 and a lower grip portion 216. Upper grip portion 214 and lower grip portion 216 define an internal cavity 218 that extends longitudinally through actuation handle 204. In some embodiments, a fluid lumen (not shown) may be positioned in internal cavity 218 for irrigated configurations. Upper grip portion 214 and lower grip portion 216 may be held together by a slip washer (not shown), a compression ring (not shown), and a handle cap 217 that threads onto the distal ends of upper grip portion 214 and lower grip portion 216. An assembly ring 219 may be positioned at the proximal end of upper grip portion 214 and lower grip portion 216 to further hold the portions together.

Figure 5:
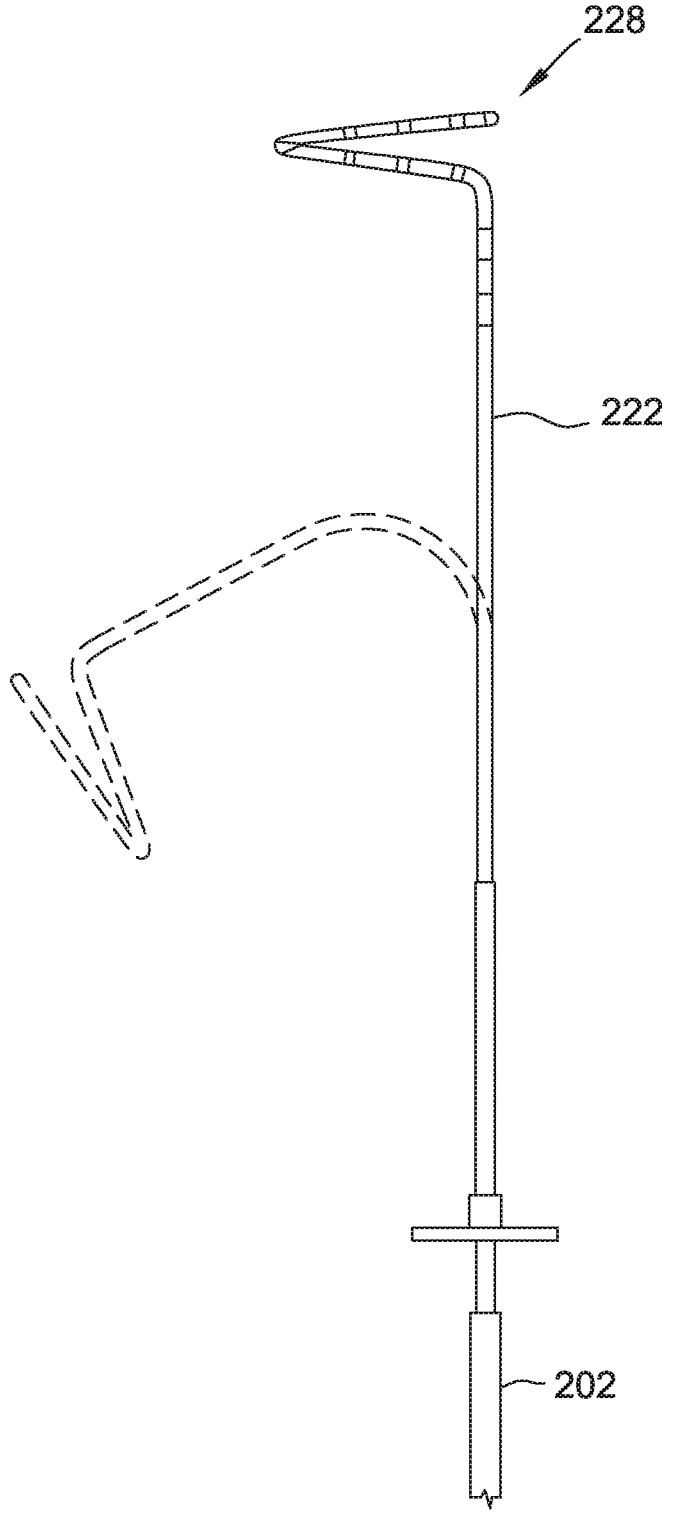
FIG. 5 is a perspective view of a catheter shaft of the catheter shown in FIG. 2 illustrating a deflectable distal portion of the catheter shaft in different positions.

Shaft 202 has a proximal end 220 coupled to actuation handle 204 and a distal end 222. In some embodiments, distal end 222 of shaft 202 is deflectable and actuation handle 204 is adapted to control deflection of deflectable distal end 222. For example, as shown in FIG. 5, distal end 222 of shaft 202 is deflectable in only a single direction (e.g., to the left as shown in FIG. 5). Accordingly, catheter 200 is a unidirectional catheter. In other embodiments, the catheter is a bidirectional catheter (i.e., the tip is deflectable in two, opposing directions).

While a variety of materials can be used to construct shaft 202, it is typically constructed of polyurethane, nylon or any suitable electrically non-conductive material. The shaft 202 serves as at least a portion of the blood contacting segment of the catheter 200 and is vascularly inserted into a patient by methods and means well known in the art.

Catheter 200 may further include a wire connector or interface, and one or more sensors, such as, for example and without limitation, a plurality of electrodes 226 (shown in FIG. 6), mounted in or on shaft 202 of catheter 200 at or near distal end 222 of shaft 202. Distal end 222 of catheter 200 may include a distal loop subassembly, such as distal loop subassembly 228.

In other embodiments, catheter 200 may further include other conventional components such as, for example and without limitation, steering wires and actuators, irrigation lumens and ports, pressure sensors, contact sensors, temperature sensors, additional electrodes and corresponding conductors or leads, and/or ablation elements (e.g., ablation electrodes, high intensity focused ultrasound ablation elements, and the like).

Figure 6:
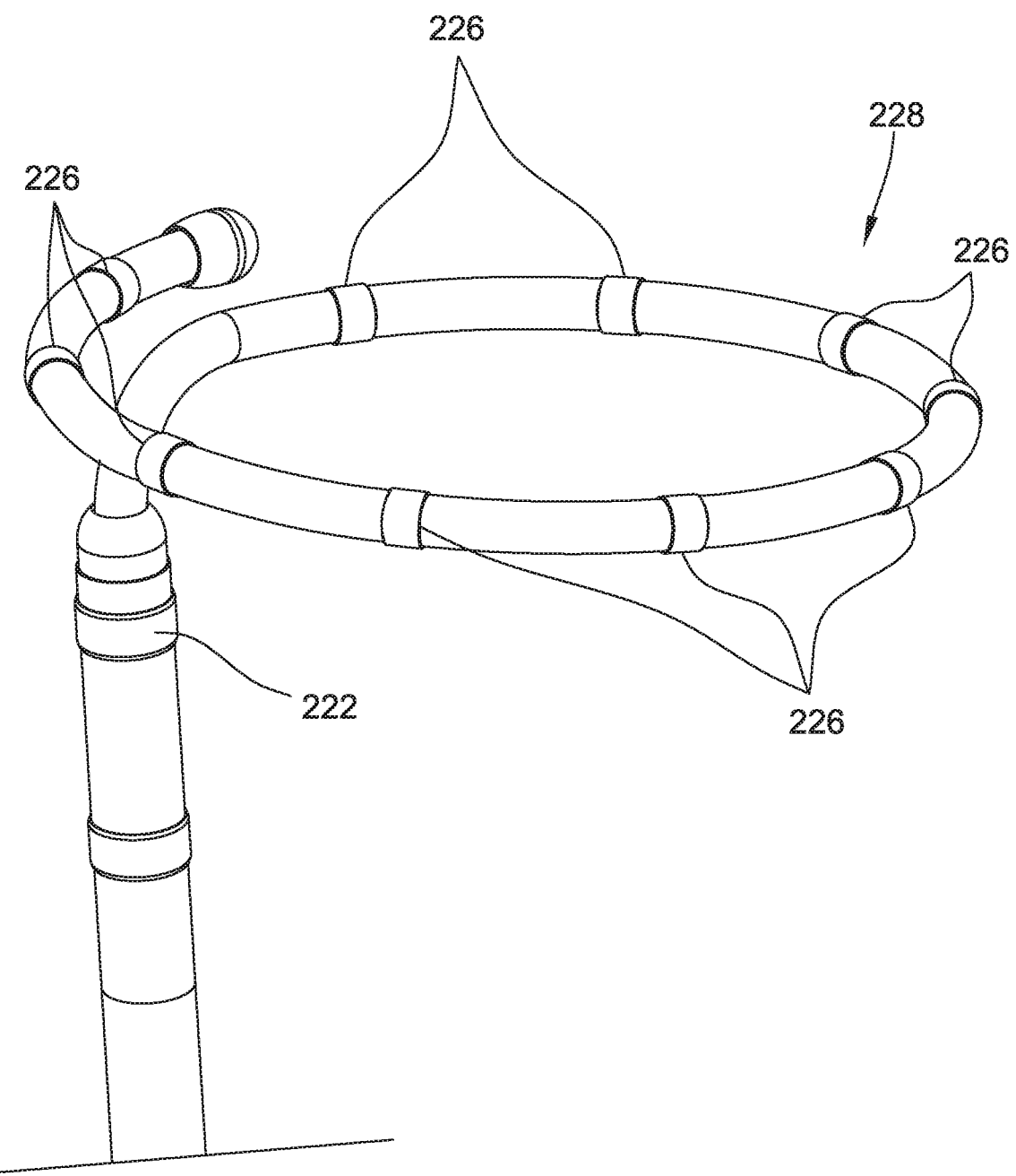
FIG. 6 is a perspective view of an electrode loop assembly of the catheter shown in FIG. 2.
Figure 7:
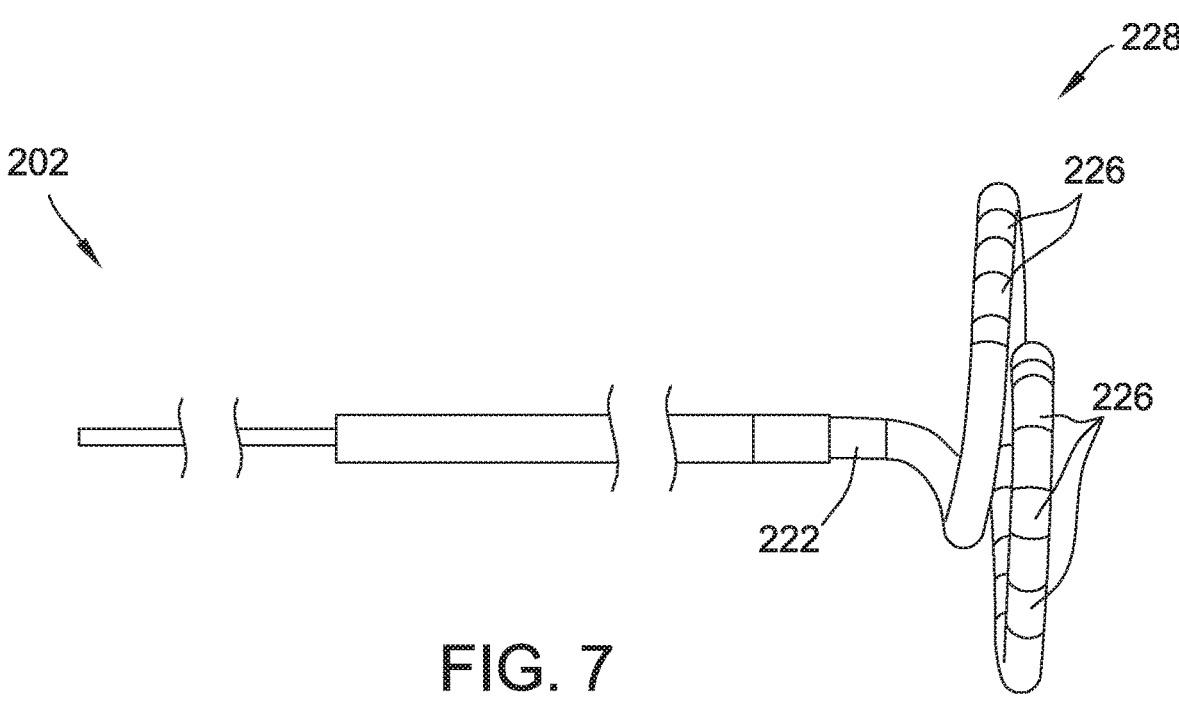
FIG. 7 is a side view of the electrode loop assembly shown in FIG. 6.
Figure 8:
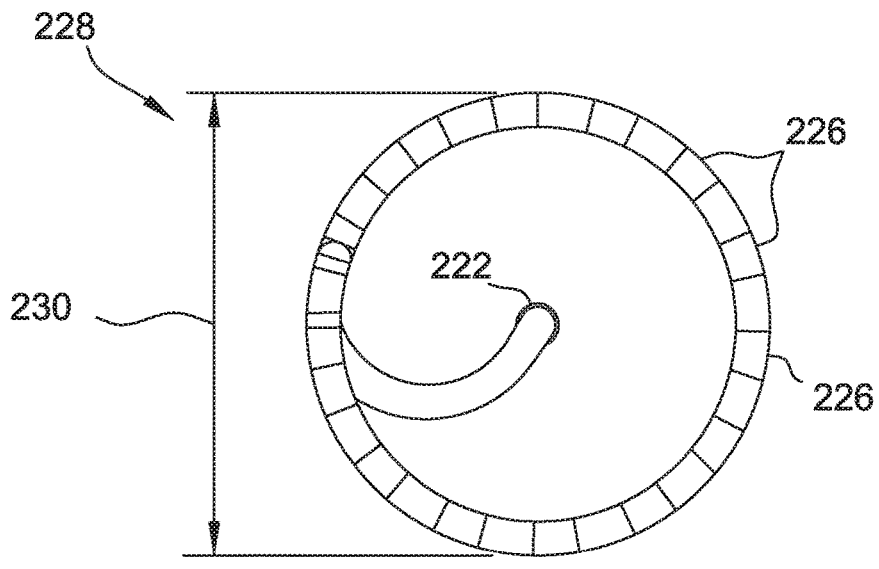
FIG. 8 is an end view of the electrode loop assembly shown in FIGS. 6 and 7.

Referring to FIGS. 6-8, in some aspects, distal end 222 of shaft 202 includes distal loop subassembly 228. A diameter of distal loop subassembly 228 may be variable in some embodiments. For example, distal loop subassembly 228 has a diameter 230 transitionable between an expanded (also referred to as "open") diameter (shown in FIG. 8) and a retracted (also referred to as "closed") diameter (not shown). In the example embodiment, the expanded diameter is approximately twenty seven mm and the retracted diameter is approximately fifteen mm. In other embodiments, diameter 230 may be variable between any suitable open and closed diameters. Alternatively, in other embodiments of the present disclosure, the diameter of distal loop subassembly 228 may be fixed.

In at least some embodiments where the diameter is variable, catheter 200 includes a loop member adjustment assembly or mechanism (e.g., a first actuator 232 shown in FIGS. 3 and 4) for allowing an operator to adjust the diameter of distal loop subassembly 228; that is, an assembly or mechanism to increase or decrease the diameter of distal loop subassembly 228. This diameter adjustment of distal loop subassembly 228 may be done at any time during a procedure, and may further be done with or without deflection of the distal end of catheter 200; that is, any deflection of the distal end is independent of any diameter adjustment of distal loop subassembly 228 in accordance with the present disclosure. This independent adjustment may be achieved through the use of multiple pull wires contained within catheter 200, for example, as described in U.S. Pat. App. Pub. No. 2017/0291008 entitled "Mapping Variable Loop Catheter Handle", the disclosure of which is incorporated herein by reference in its entirety. By having the capability to adjust the diameter of distal loop subassembly 228 before or during a procedure, an operator may be able to more effectively navigate the vasculature of a patient as described herein and improve patient outcomes as noted above.

As shown in FIGS. 6-8, the plurality of catheter electrodes 226 mounted on distal loop subassembly 228 may be used for a variety of diagnostic and therapeutic purposes including, for example and without limitation, cardiac mapping and/or ablation. For example, one or more of catheter electrodes 226 may perform a location or position sensing function. More particularly, one or more of catheter electrodes 226 may be configured to be a positioning sensor(s) that provides information relating to the location (position and orientation) of distal loop subassembly 228.

Referring again to FIGS. 2-4, a wire connector, such as wire connector 110 shown in FIG. 1, may be at proximal end 208 of actuation handle 204. Actuation handle 204 can also include a strain relief 238 at distal end 210. In embodiments including electrodes, such as electrodes 226 on distal loop subassembly 228 shown in FIG. 6, each electrode 226 may be connected to an electrical conductor wire that extends to the wire connector through shaft 202, strain relief 238, and actuation handle 204. The wire connector is adapted to be connected to a device, such as a recording, monitoring, or RF ablation device.

In the illustrated embodiment, a connector shield 242 is positioned in internal cavity 218 and configured to house at least one electrical component or terminal connected to conductor wire. Connector shield 242 is separate from housing 206 and is positioned within internal cavity 218. Connector shield 242 includes a sidewall 244 extending around longitudinal axis 212. Sidewall 244 defines a keyhole 246 that engages a key on housing 206 to retain the axial position of connector shield 242 within internal cavity 218. Connector shield 242 is constructed of a material that prevents magnetic fields from interfering with the electronic components housed within connector shield 242. In other embodiments, connector shield 242 may be constructed as an integral portion of housing 206 instead of as a separate piece from housing 206.

Actuation handle 204 can include a first actuator 232 and a second actuator 234. First actuator 232 is movably coupled to grip portions 214, 216 in such a manner that first actuator 232 may rotate around the circumference of actuation handle 204. Second actuator 234 is movably coupled to grip portions 214, 216 in such a manner that second actuator 234 may slide along grip portions 214, 216 in a direction that is generally parallel to longitudinal axis 212 of actuation handle 204. Displacement of first actuator 232 and second actuator 234 allows a user to vary diameter of distal loop subassembly 228 and deflect distal end 222 of shaft 202, respectively. For example, as indicated in FIG. 2, in one embodiment where distal end 222 forms a loop or lariat, first actuator 232 causes distal end 222 to increase or decrease the diameter of distal loop subassembly 228, and second actuator 234 causes distal end 222 to deflect in at least one direction. In other embodiments, first actuator 232 causes distal end 222 to deflect in at least one direction, and second actuator 234 causes distal end 222 to increase or decrease the diameter of distal loop subassembly 228.

Figure 9:
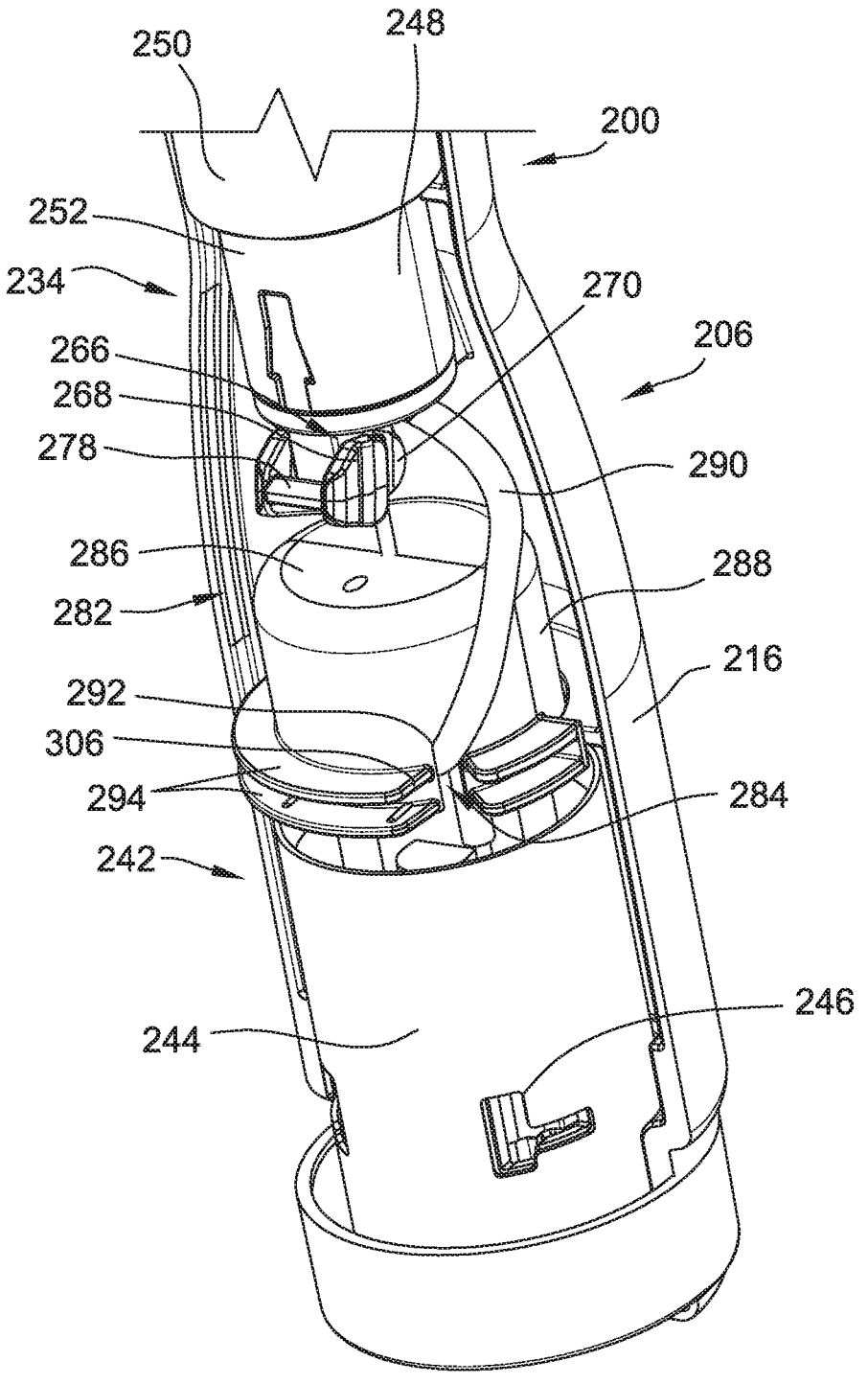
FIG. 9 is an enlarged perspective view of a portion of the internal cavity of the catheter shown in FIG. 2, illustrating a wire extending alongside a wire management cap and into a wire receiver cavity defined by the wire management cap.

With additional reference to FIG. 9, second actuator 234 includes a plunger assembly 248 including a plunger body 252 slidably mounted in at least one sleeve bearing 250 and a plunger cap 254 at a proximal end of plunger assembly 248. Also, a thumb boss 258 threads onto distal end of plunger body 252. A gripper 262 including a wire anchor 264 is attached on a mid-section of plunger body 252 and operatively connected to distal end 222 of shaft 202 by a wire extending through actuation handle 204 and shaft 202. During operation of catheter 200, an operator may displace plunger assembly 248 by contacting thumb boss 258 and thereby siding plunger assembly along longitudinal axis 212 of actuation handle 204. Sliding displacement of plunger assembly 248 along longitudinal axis 212 of actuation handle 204 causes displacement of distal end 222 of shaft 202 as shown in FIG. 4.

Figure 10:
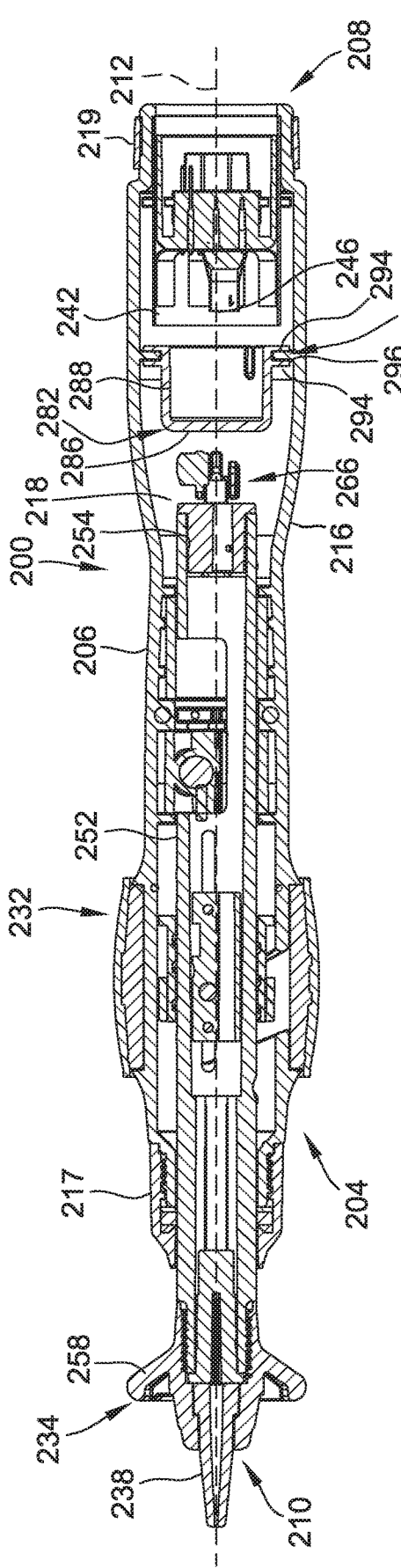
FIG. 10 is a cross-sectional view of the catheter handle shown in FIG. 2.
Figure 11:
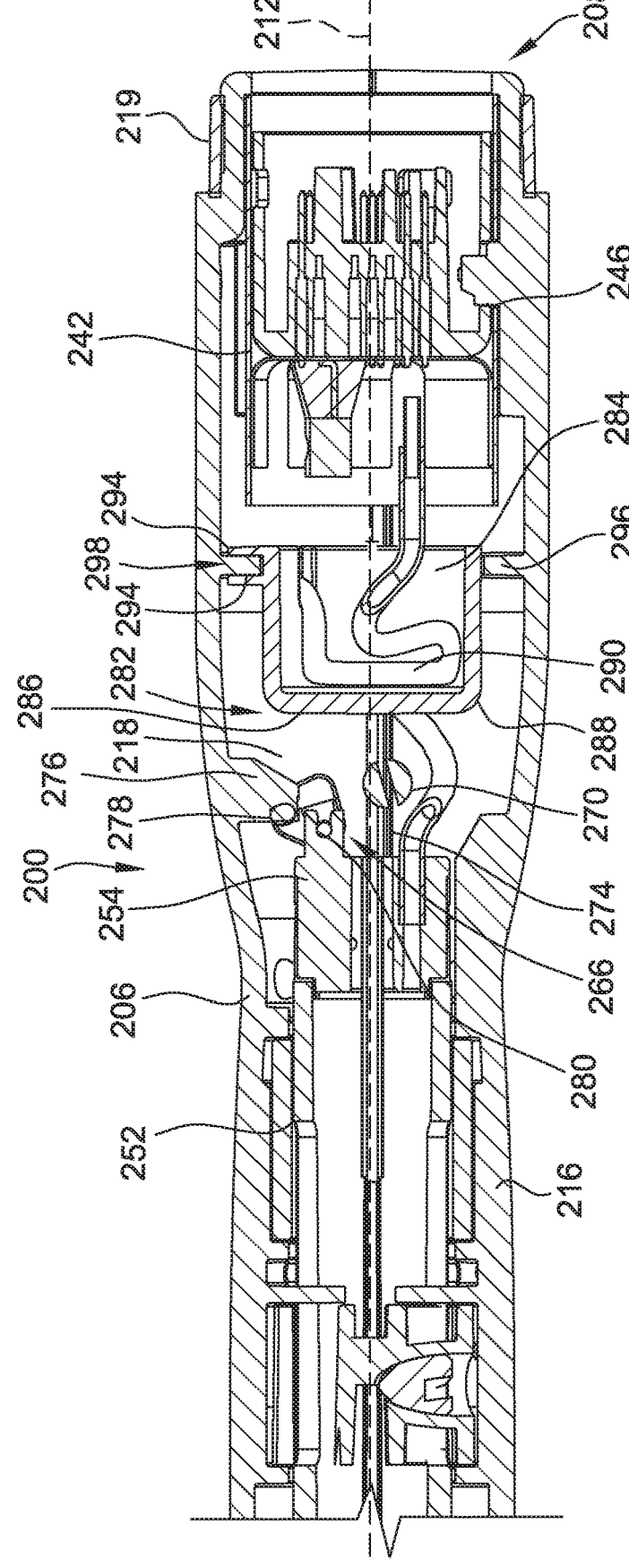
FIG. 11 is an enlarged cross-sectional view of a portion of the catheter handle shown in FIG. 2.
Figure 12:
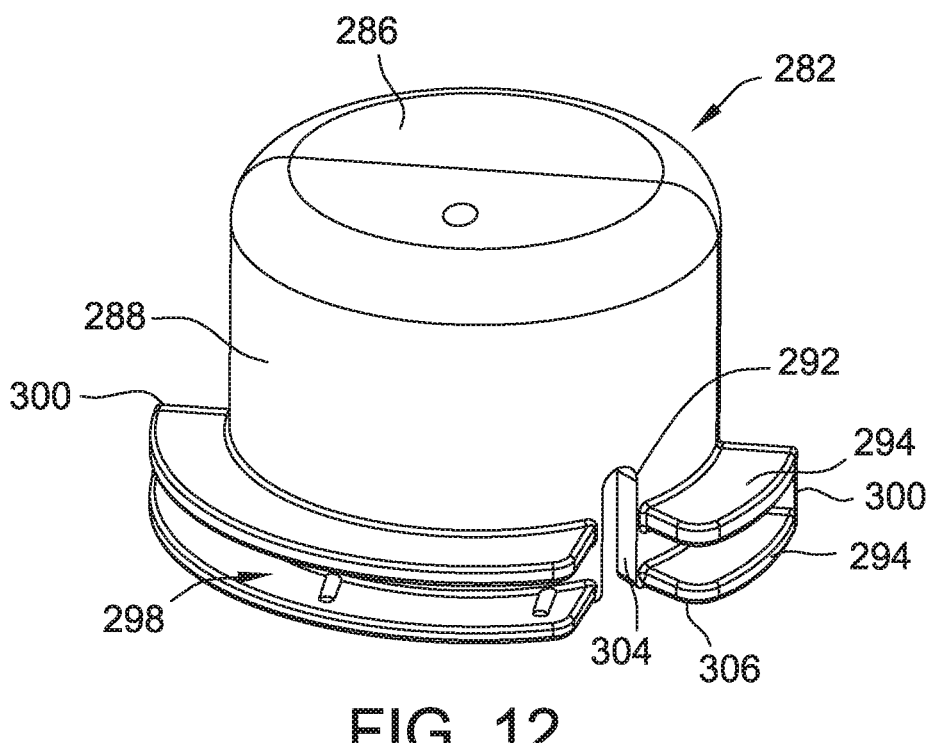
FIG. 12 is a perspective view of a wire management cap of the catheter shown in FIG. 2.
Figure 13:
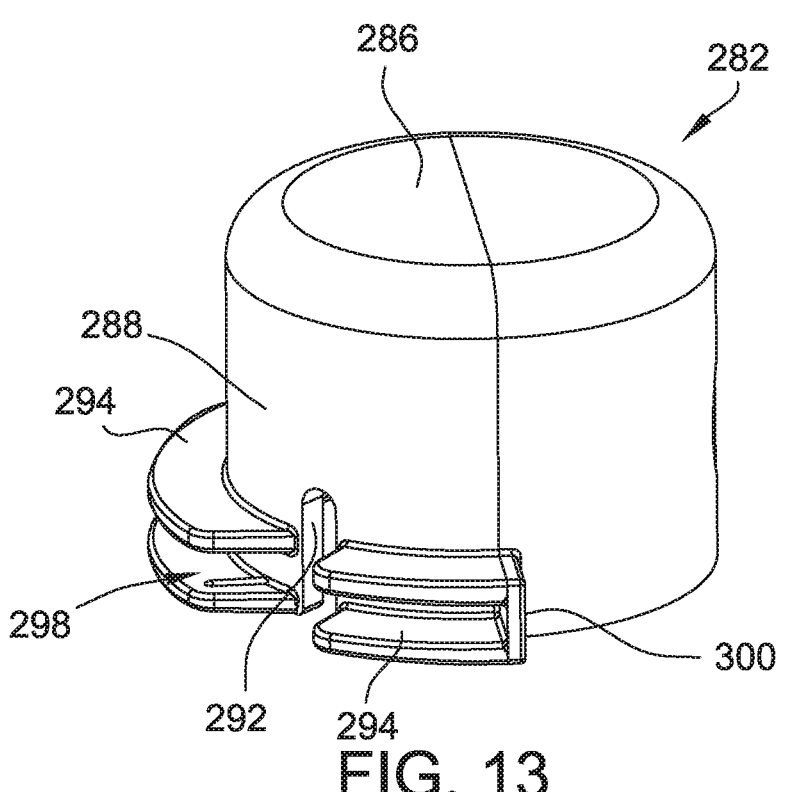
FIG. 13 is another perspective view of the wire management cap shown in FIG. 12.
Figure 14:
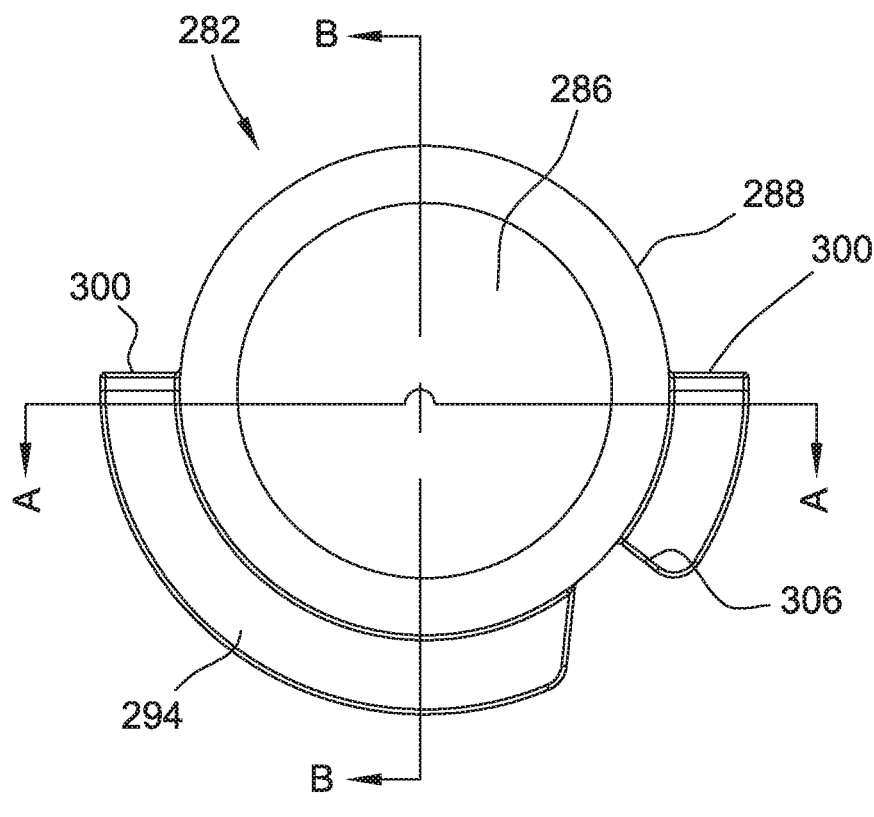
FIG. 14 is an end view of a closed end of the wire management cap shown in FIG. 12.
Figure 15:
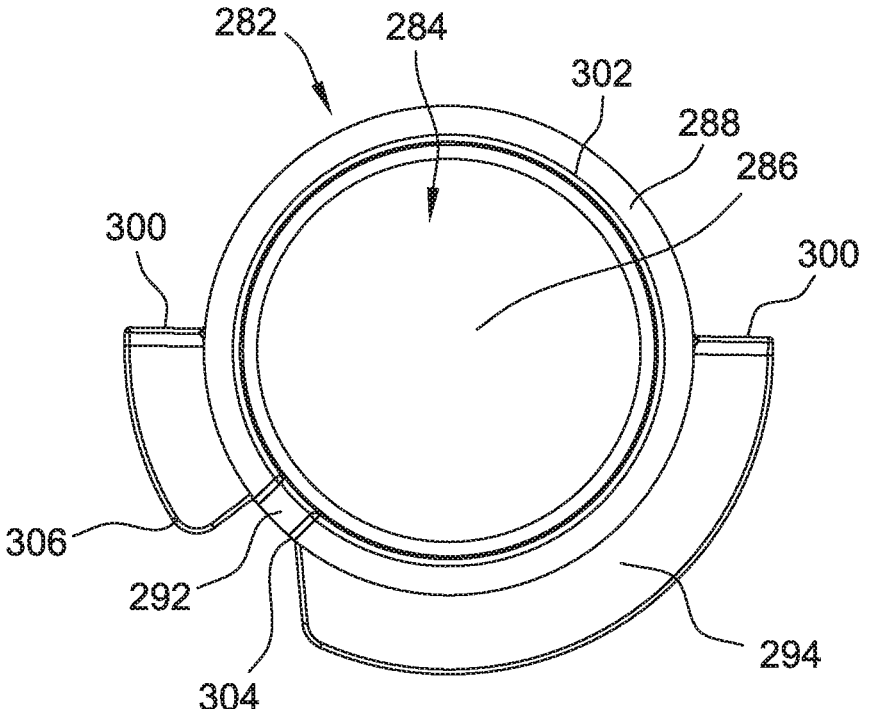
FIG. 15 is an end view of an open end of the wire management cap shown in FIG. 12.
Figure 16:
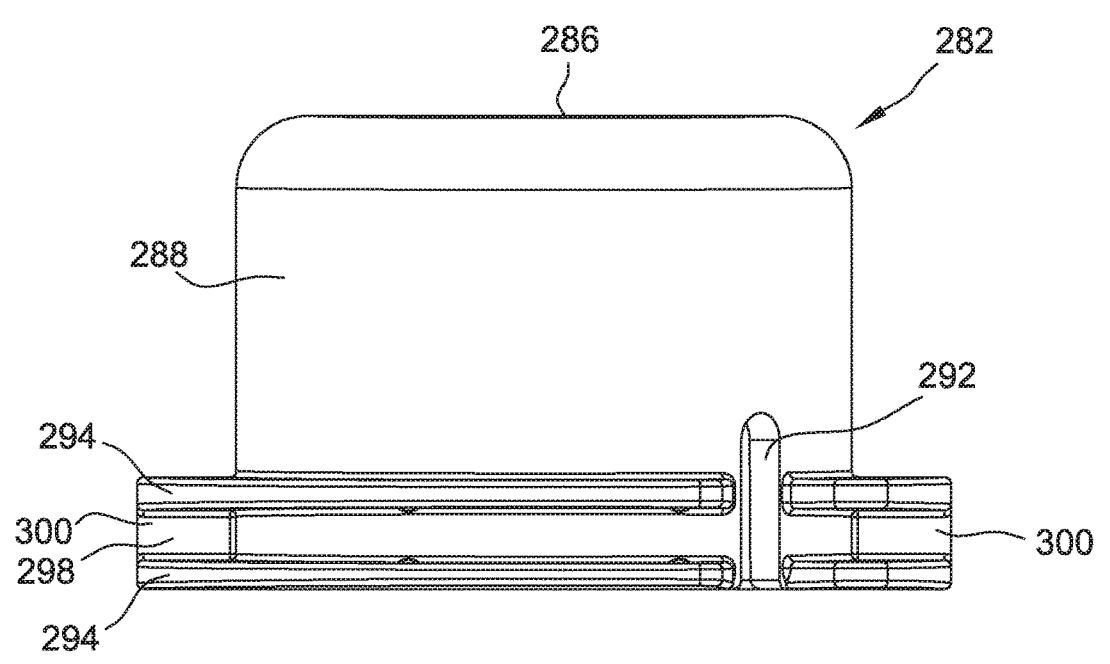
FIG. 16 is a side view of the wire management cap shown in FIG. 12.
Figure 17:
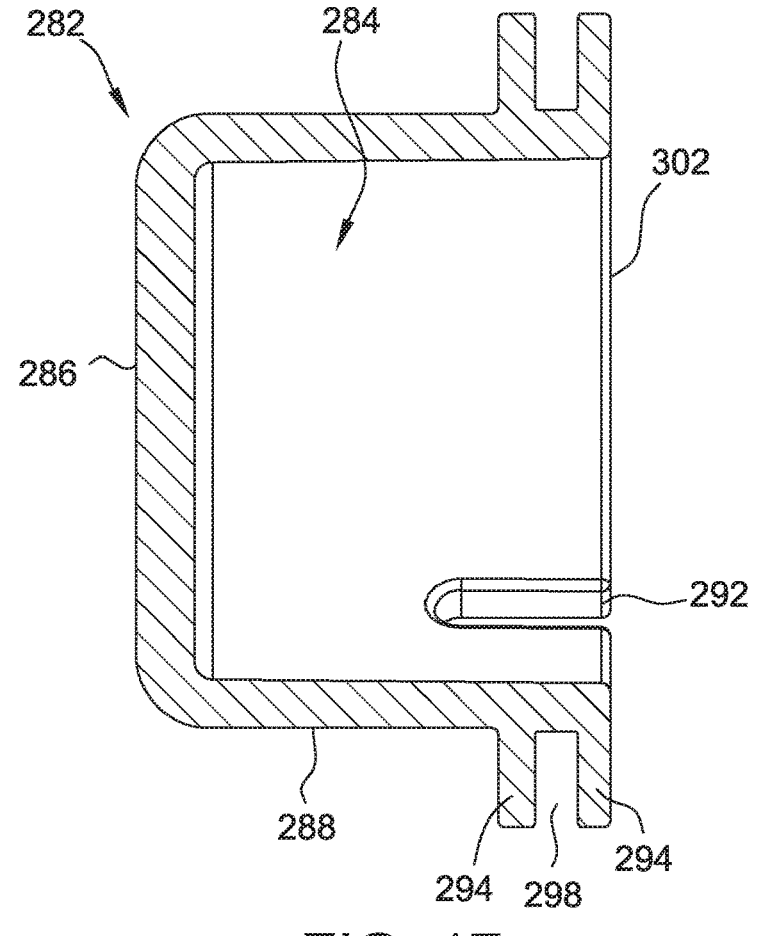
FIG. 17 is a cross-sectional view of the wire management cap shown in FIG. 12, taken along line A-A shown in FIG. 14.

As shown in FIGS. 9-11, second actuator 234 further includes a return-to-straight mechanism 266. Return-to-straight mechanism 266 includes a lever 268 that switches between an unactuated configuration and an actuated configuration. Lever 268 is pivotably mounted to the proximal side of plunger cap 254 (FIG. 4). In some embodiments, a lever tuner 270 is threaded into a tuner drum of lever 268 to attach lever 268 to a deflection element 274 connected to plunger cap 254. Deflection element 274 is configured to displace plunger assembly 248 when lever 268 is in the actuated configuration. In the unactuated configuration, lever 268 is spaced apart from an actuation boss 276 on housing 206. When plunger assembly 248 is fully retracted, return-to-straight mechanism 266 is switched to the actuated configuration. Specifically, when plunger assembly is fully retracted, actuation boss 276 mounted on housing 206 is engaged with an actuation pin 278 of lever 268, thereby pivoting lever 268 about a pivot pin 280 and moving tuner drum away from the plunger cap 254 and pulling deflection element 274 proximally to thereby fully straighten distal end 222 of shaft 202 to the substantially straight configuration shown in FIGS. 2 and 3.

First actuator 232 and second actuator 234 may be connected to deflectable distal end 222 of shaft 202 by actuation wires. The actuation wires can be any of the actuation wire types known in the art. They can be pull or tension wires (i.e., the actuation wires are not adapted to support a compressive load). They can also be configured such that the actuation wires are pull/push or tension/compression wires (is, the actuation wires are adapted to support a compressive load). Thus, in the context of the first and second actuation wires, when one actuation wire is placed in tension, the other actuation wire will carry a compressive load. The actuation wires can be formed from a super elastic Nitinol wire or another suitable material.

Referring to FIG. 9, actuation handle 204 includes one or more wires extending through internal cavity 218 between proximal end 220 and distal end 222. For example, the wires may extend between the electrodes 226 (shown in FIG. 2) and a connector such as the connector 110 shown in FIG. 1. The wires may extend alongside movable components such as return-to-straight mechanism 266 of second actuator 234. Actuation handle 204 includes one or more wire management features that retain the wires in position in internal cavity 218 and prevent interference between the wire and the movable component. For example, in the illustrated embodiment, actuation handle 204 includes a wire management cap 282 within internal cavity 218. In the illustrated embodiment, wire management cap 282 is positioned between return-to-straight mechanism 266 and proximal end 208 of actuation handle 204, although wire management cap 282 may be positioned at any other suitable location within internal cavity 218.

Wire management cap 282 defines a wire receiver cavity 284 sized to receive a portion of the wire therein. In some embodiments, one or more of the wires are positioned within a sleeve or tube 290 which protects the wire and/or allows grouping of two or more wires together. In such embodiments, sleeve 290 with the wire inside may be positioned within the wire management cap 282. A portion of the wire may be positioned in the wire receiver cavity by bending the wire into a circular shape, i.e., a loop, and positioning the portion within the wire receiver cavity 284. As used with respect to the wire management cap 282 and wires housed therein, the term "loop" refers to a curved portion of wire that may or may not overlap itself at least once. For example, slack portions of the wire, e.g., the extra length of wire that allows the wire to extend greater than the straight-line distance between components for connection to the components, may be gathered in the wire receiver cavity 284 such that the wire extends tautly through internal cavity 218. Moreover, wire management cap 282 is oriented such that the portion of the wire in wire receiver cavity 284 is separated from one or more movable components by wire management cap 282 to prevent interference between the movable components and the wire. For example, in the illustrated embodiment, wire management cap 282 is positioned between connector shield 242 and return-to-straight mechanism 266 of second actuator 234. Moreover, wire management cap 282 is oriented such that wire receiver cavity 284 is open to the connector shield 242 to allow wires to extend from the wire receiver cavity 284 to one or more connectors within connector shield 242.

Wire management cap 282 includes an end wall 286 extending transversely across internal cavity 218 between second actuator 234 and proximal end 220 of actuation handle 204. Wire management cap 282 also includes a sidewall 288 extending proximally from an edge of the end wall 286. End wall 286 and sidewall 288 cooperatively define wire receiver cavity 284.

Also, sidewall 288 defines at least one slot 292 extending axially from an open end of wire management cap 282. In the illustrated embodiment, at least one wire or wire-containing sleeve 290 extends through slot 292 and into wire receiver cavity 284. Slot 292 is sized to receive and retain the wire or wire-containing sleeve 290 therein. Accordingly, slot 292 may facilitate orienting the wire at a desired position within internal cavity 218. In addition, slot 292 may simplify assembly of catheter 200 because slot 292 provides a visible indication where to feed the wire into wire receiver cavity 284 of wire management cap 282. In addition, sidewall 288 retains wire within slot 292 and wire receiver cavity 284 of wire management cap 282 as wire management cap 282 is positioned within internal cavity 218 and attached to housing 206.

In the illustrated embodiment, wire management cap 282 is a separate piece from housing 206 and is configured to attach to housing 206. For example, wire management cap 282 includes a pair of axially-spaced apart flanges 294 that extend circumferentially around sidewall 288. Flanges 294 are configured to engage a rib 296 of housing 206 to axially fix wire management cap 282 to housing 206. Specifically, flanges 294 define a channel 298 that receives rib 296 of housing 206 between flanges 294. The width of channel 298 is smaller than the thickness of rib 296 such that rib 296 forms an interference fit with flanges 294. Rib 296 may extend from one or both of lower grip portion 216 and upper grip portion 214.

As a result, wire management cap 282 is able to attach to housing 206 without the use of tools and without requiring other attachment means such as adhesives and fasteners. In addition, the engagement between wire management cap 282 and housing 206 reduces movement of wire management cap 282 relative to housing 206 during operation of catheter 200. Also, wire management cap 282 is modular and is able to be used with different catheter handles, such as catheter handles for unidirectional or bidirectional catheters, because wire management cap 282 is modular and is a separate piece from housing 206. Consequently, wire management cap 282 may be retrofitted on at least some existing catheter handles.

Referring to FIGS. 12-17, in the illustrated embodiment, end wall 286 is circular and sidewall 288 extends completely around the circumference of end wall 286 at the outer edge of end wall 286. In addition, sidewall 288 defines an open end 302 opposite closed end defined by end wall 286. Accordingly, wire management cap 282 is an open-ended cylinder. The shape of wire management cap 282 facilitates wire management cap 282 receiving and retaining portions of the wires because the wires can be curved into a loop with a diameter that corresponds to the diameter of the wire receiver cavity 284. Moreover, the wire management cap 282 is modular and is compatible with a variety of catheter handles such that wire management cap 282 can be retrofitted onto other catheter handles.

In the exemplary embodiment, wire management cap 282 is formed as a single piece. In other words, end wall 286 and sidewall 288 are integrally joined together. Also, in the illustrated embodiment, wire management cap 282 has substantially smooth surfaces and rounded corners such that wire management cap 282 is free of relatively sharp edges to contact wires. In some embodiments, wire management cap 282 may be a molded plastic piece. In other embodiments, wire management cap 282 may be formed other than as a single piece.

Sidewall 288 defines slot 292 extending distally from open end 302. Slot 292 is sized to permit at least one wire or wire-containing sleeve 290 (shown in FIG. 9) to extend therethrough and into wire receiver cavity 284. Specifically, edges 304 of sidewall 288 define slot 292 and have an inverted U-shape. In addition, edges 304 are rounded to prevent damage to the wires extending through slot 292 and allow the wires to be retained in slot 292. The wires may be positioned axially along sidewall 288 of wire management cap 282 from end wall 286 to slot 292. The width of slot 292 is approximately equal to or slightly less than the diameter of the wire or wire-containing sleeve 290 (shown in FIG. 9). In addition, slot 292 has a length that is greater than the cumulative diameter of at least two wires such that multiple wires can be positioned in slot 292 together.

The wire management cap 282 further includes flanges 294 extending radially outward from sidewall 288 and configured to engage housing 206 (shown in FIG. 10) to axially fix wire management cap 282 to housing 206. Specifically, in the illustrated embodiment, wire management cap 282 includes a pair of flanges 294 extending around sidewall 288 and configured to engage rib 296 (shown in FIG. 10) of housing 206 (shown in FIG. 10) to axially fix wire management cap 282 to housing 206. In the illustrated embodiment, flanges 294 extend less than the full circumference of sidewall 288, and the width of channel 298 between flanges 294 is substantially equal to the width of rib

296 on one of lower grip portion 216 and upper grip portion 214. In some embodiments, stops 300 extend across opposed ends of channel 298 between flanges 294 and limit rotation of wire management cap 282 relative to housing 206.

Each flange 294 has a gap 306 defined therein that is radially and circumferentially aligned with slot 292 to allow the wire to be routed alongside sidewall 288 and into wire receiver cavity 284 through slot 292 without obstructing the engagement of flanges 294 and housing 206 (shown in FIG. 10). Also, wire management cap 282 is configured to confine the wire between sidewall 288 and housing 206 when wire management cap 282 is coupled to housing 206.

Figure 18:
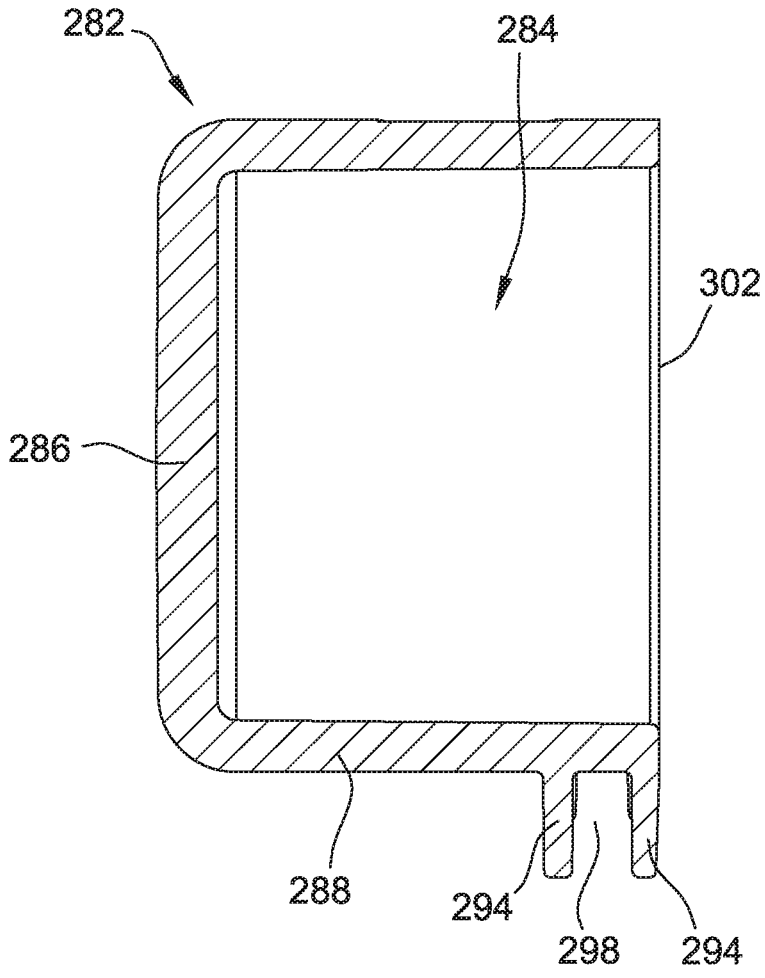
FIG. 18 is a cross-sectional view of the wire management cap shown in FIG. 12, taken along line B-B shown in FIG. 14.

FIG. 18 is a flow diagram illustrating one embodiment of a method 1100 of assembling a catheter handle (e.g., handle 204 shown in FIG. 2). Method 1100 includes positioning 1102 a wire in an internal cavity (e.g., cavity 218) defined by a housing (e.g., housing 206) of the catheter handle. The wire extends alongside at least one movable component (e.g., return-to-straight mechanism 266) positioned within internal cavity 218.

The method 1100 also includes positioning 1104 a wire management cap (e.g., wire management cap 282) in the internal cavity between the movable component and one of a proximal end and a distal end of the catheter handle. The wire management cap includes an end wall (e.g., end wall 286) extending at least in part transversely across the internal cavity and defines a wire receiver cavity (e.g., wire receiver cavity 284). In some embodiments, the housing is formed by connecting a first grip portion (upper grip portion 214) to a second grip portion (e.g., lower grip portion 216) to define the internal cavity therebetween. For example, the wire management cap and other components of the catheter handle may be connected to the first grip portion in a desired axial position and the second grip portion may be connected to the first grip portion to enclose the components in the internal cavity.

The method 1100 further includes positioning 1106 a portion of the wire in the wire receiver cavity of the wire management cap. For example, the wire may be positioned through a slot (e.g., slot 292) in the wire management cap and into the wire receiver cavity.

In some embodiments, the method 1100 includes engaging an engagement feature (e.g. flanges 294) of the wire management cap and an engagement feature (e.g., rib 296) of the housing to axially fix the wire management cap to the housing. The wire management cap may be positioned between a connector shield (e.g., connector shield 242) and the movable component. In addition, the wire management cap is oriented such that the portion of the wire in the wire receiver cavity is separated from the movable component by the wire management cap to prevent interference between the movable component and the wire.

Although certain steps of the example method are numbered, such numbering does not indicate that the steps must be performed in the order listed. Thus, particular steps need not be performed in the exact order they are presented, unless the description thereof specifically require such order. The steps may be performed in the order listed, or in another suitable order.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the invention, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A catheter handle comprising:
a housing extending from a proximal end to a distal end along a longitudinal axis, the housing defining an internal cavity;
at least one wire extending through the internal cavity between the proximal end and the distal end; and
a wire management cap positioned within the internal cavity between a movable component of the catheter handle and one of the proximal and distal ends, wherein the wire management cap comprises a sidewall at least partially defining a wire receiver cavity, wherein the sidewall defines a slot therein, wherein the at least one wire is routed through the slot into the wire receiver cavity such that at least a portion of the wire is received in the wire receiver cavity, and wherein the wire management cap is oriented such that the portion of the wire in the wire receiver cavity is separated from the movable component by the wire management cap to prevent interference between the movable component and the wire.

2. The catheter handle of claim 1, wherein the wire management cap comprises an end wall extending transversely across the internal cavity between the movable component and the one of the proximal and distal ends.

3. The catheter handle of claim 2, wherein the sidewall extends from the end wall and defines an open end opposite the end wall, the end wall and sidewall cooperatively defining the wire receiver cavity.

4. The catheter handle of claim 3, wherein the sidewall defines the slot extending from the open end.

5. The catheter handle of claim 1, wherein the wire management cap further comprises at least one flange extending radially outward from the sidewall and configured to engage the housing to axially fix the wire management cap to the housing, wherein the at least one flange has a gap defined therein that is radially aligned with the slot.

6. The catheter handle of claim 3, wherein the end wall is circular and the sidewall extends around the circumference of the end wall to form a cylinder, the wire management cap further comprising a pair of flanges extending around the sidewall and configured to engage a rib of the housing to axially fix the wire management cap to the housing.

7. The catheter handle of claim 1, wherein the wire management cap is a separate piece from the housing and is configured to attach to the housing.

8. The catheter handle of claim 1 further comprising an actuator assembly including the movable component and disposed in the internal cavity, wherein the actuator assembly is coupled to a catheter shaft.

9. The catheter handle of claim 1 further comprising a connector shield positioned in the internal cavity, the connector shield configured to house at least one terminal connection of the wire, wherein the wire management cap is positioned between the connector shield and the movable component.

10. A catheter comprising:
a handle extending from a proximal end to a distal end along a longitudinal axis, the handle comprising a housing defining an internal cavity;
a catheter shaft attached to the distal end of the handle, the catheter shaft comprising at least one wire that extends into and through the internal cavity;
an actuator assembly including at least one movable component disposed in the internal cavity; and
a wire management cap positioned within the internal cavity, wherein the wire management cap comprises a sidewall at least partially defining a wire receiver cavity, wherein the sidewall defines a slot therein, wherein the at least one wire is routed through the slot into the wire receiver cavity such that at least a portion of the wire is received in the wire receiver cavity, and wherein the wire management cap is oriented such that the portion of the wire in the wire receiver cavity is separated from the movable component by the wire management cap to prevent interference between the movable component and the wire.

11. The catheter of claim 10 further comprising a connector shield positioned in the internal cavity, the connector shield configured to house at least one terminal connection of the wire, wherein the wire management cap is positioned between the connector shield and the movable component.

12. The catheter of claim 10, wherein the wire management cap comprises an end wall extending transversely across the internal cavity and the sidewall extends from the end wall and defines an open end opposite the end wall, the end wall and sidewall cooperatively defining the wire receiver cavity.

13. The catheter of claim 12, wherein the sidewall defines the slot extending from the open end.

14. The catheter of claim 10, wherein the wire management cap further comprises at least one flange extending radially outward from the sidewall and configured to engage the housing to axially fix the wire management cap to the housing, wherein the at least one flange has a gap defined therein that is radially aligned with the slot.

15. The catheter of claim 12, wherein the end wall is circular and the sidewall extends around the circumference of the end wall to form a cylinder, the wire management cap further comprising a pair of flanges extending around the sidewall and configured to engage a rib of the housing to axially fix the wire management cap to the housing.

16. A method of assembling a catheter handle, the method comprising:
positioning a wire in an internal cavity defined by a housing of the catheter handle, the wire extending alongside at least one movable component positioned within the internal cavity;
positioning a wire management cap in the internal cavity between the movable component and one of a proximal end and a distal end of the catheter handle, the wire management cap comprising a sidewall at least partially defining a wire receiver cavity, wherein the sidewall defines a slot therein;
routing the wire through the slot into the wire receiver cavity; and

positioning a portion of the wire in the wire receiver cavity, wherein the wire management cap is oriented such that the portion of the wire in the wire receiver cavity is separated from the movable component by the wire management cap to prevent interference between the movable component and the wire.

17. The method of claim 16 further comprising engaging flanges of the wire management cap and a rib of the housing to axially fix the wire management cap to the housing.

18. The method of claim 16, wherein the housing includes a first grip portion and a second grip portion, the method further comprising attaching the wire management cap to one of the first grip portion and the second grip portion and connecting the first grip portion and the second grip portion to define the internal cavity.

19. The method of claim 16 further comprising attaching a proximal end of a catheter shaft to the catheter handle and attaching an actuator including the movable component to the catheter handle, wherein the actuator is configured to deflect a portion of the catheter shaft.

\* \* \* \* \*